(12) United States Patent
Sokolovskii et al.

(10) Patent No.: US 10,137,437 B2
(45) Date of Patent: Nov. 27, 2018

(54) METHOD FOR PRODUCING A CATALYST FOR THE PARTIAL OXIDATION/AMMOXIDATION OF OLEFINS

(71) Applicant: Clariant Corporation, Louisville, KY (US)

(72) Inventors: Valery Sokolovskii, Santa Clara, CA (US); David Michael Lowe, Sunnyvale, CA (US); Deepti Machiraju, Mountain View, CA (US); Hongyi C. Hou, Sunnyvale, CA (US); Gerhard Mestl, Munich (DE); Claus G. Lugmair, San Jose, CA (US); Aaron B. Miller, San Ramon, CA (US); Anthony F. Volpe, Jr., Santa Clara, CA (US)

(73) Assignee: Clariant Corpoation, Louisville, KY (US)

( * ) Notice: Subject to any disclaimer, the term of this patent is extended or adjusted under 35 U.S.C. 154(b) by 222 days.

(21) Appl. No.: 14/782,878

(22) PCT Filed: Apr. 11, 2014

(86) PCT No.: PCT/US2014/033714
§ 371 (c)(1),
(2) Date: Oct. 7, 2015

(87) PCT Pub. No.: WO2014/169163
PCT Pub. Date: Oct. 16, 2014

(65) Prior Publication Data
US 2016/0051967 A1 Feb. 25, 2016

(30) Foreign Application Priority Data
Apr. 11, 2013 (DE) .................. 10 2013 006 251

(51) Int. Cl.
| | |
|---|---|
| *B01J 23/888* | (2006.01) |
| *B01J 37/02* | (2006.01) |
| *B01J 37/08* | (2006.01) |
| *B01J 23/887* | (2006.01) |
| *B01J 35/10* | (2006.01) |
| *C07C 253/26* | (2006.01) |
| *C07C 45/35* | (2006.01) |
| *B01J 23/00* | (2006.01) |
| *B01J 21/08* | (2006.01) |

(52) U.S. Cl.
CPC ......... *B01J 23/8885* (2013.01); *B01J 23/002* (2013.01); *B01J 23/8872* (2013.01); *B01J 35/1009* (2013.01); *B01J 35/1014* (2013.01); *B01J 35/1019* (2013.01); *B01J 37/0201* (2013.01); *B01J 37/0215* (2013.01); *B01J 37/08* (2013.01); *C07C 45/35* (2013.01); *C07C 253/26* (2013.01); *B01J 21/08* (2013.01); *B01J 2523/00* (2013.01); *Y02P 20/52* (2015.11)

(58) Field of Classification Search
CPC ................ B01J 23/8885; B01J 37/0215; B01J 37/0201; B01J 37/08
See application file for complete search history.

(56) References Cited

U.S. PATENT DOCUMENTS

| | | | | |
|---|---|---|---|---|
| 4,732,884 | A | * | 3/1988 | Sarumaru .............. B01J 23/002 |
| | | | | 502/205 |
| 5,834,394 | A | | 11/1998 | Chen |
| 5,856,259 | A | | 1/1999 | Watanabe |
| 6,383,973 | B1 | | 5/2002 | Kimura |
| 6,632,965 | B1 | | 10/2003 | Tanimoto |
| 6,781,013 | B2 | | 8/2004 | Tanimoto |
| 6,946,422 | B2 | | 9/2005 | Stevenson |
| 7,341,974 | B2 | | 3/2008 | Kang |
| 7,348,291 | B2 | | 3/2008 | Paparizos |
| 7,544,633 | B2 | | 6/2009 | Kang |
| 7,632,777 | B2 | | 12/2009 | Teshigahara |
| 7,851,397 | B2 | | 12/2010 | Liang |
| 8,288,306 | B2 | | 10/2012 | Luo |
| 2004/0110978 | A1 | * | 6/2004 | Paparizos .............. B01J 23/002 |
| | | | | 558/325 |
| 2007/0275849 | A1 | | 11/2007 | Shin |
| 2010/0324331 | A1 | | 12/2010 | Fischer |

FOREIGN PATENT DOCUMENTS

MY 141945 7/2010

OTHER PUBLICATIONS

Bu Young Jo, Performance of Mo12Bi1.0Co4.4Fe1.0K0.07Ox catalysts prepared from a sol-gel solution containing added ethylene glycol in the partial oxidation of propylene to acrylic acid, Appl Catal A Gen 358, (2009), 180-185.

Duc Truong Duc, Selective oxidation of propylene to acrolein by silica-supported bismuth molybdate catalysts, Res Chem Intermed 37, (2011), 605-616.

\* cited by examiner

*Primary Examiner* — Joseph R Kosack

(57) ABSTRACT

The present invention relates to a method for producing a supported catalyst, a catalyst which is obtainable using the method, and use thereof for the partial oxidation or ammoxidation of olefins, in particular for the oxidation of propene to acrolein, of isobutene to methacrolein, and/or the ammoxidation of propene to acrylonitrile. The method according to the invention includes the following steps: a) providing a solution in which precursor compounds of the catalytically active component are essentially completely dissolved in a suitable solvent; b) bringing the solution obtained in step a) into contact with a (chemically) inert, porous support having a specific surface of 1 to 500 m²/g; c) heat treatment of the material obtained in step b), in which the precursor compounds of the catalytically active component are converted to their oxides.

20 Claims, No Drawings

METHOD FOR PRODUCING A CATALYST FOR THE PARTIAL OXIDATION/AMMOXIDATION OF OLEFINS

The present invention relates to a simple method for producing a supported catalyst, a catalyst which is obtainable using the method, and use thereof for the partial oxidation or ammoxidation of olefins, in particular for the oxidation of propene to acrolein, of isobutene to methacrolein, and/or the ammoxidation of propene to acrylonitrile.

The partial oxidation of propene to acrolein, of isobutene to methacrolein, and the ammoxidation of propene to acrylonitrile are widely used industrially as the first step in the production of acrylic acid, acrylic esters, and acrylamide or methacrylic acid, which in turn are important intermediate products in the production of acrylic polymers such as poly(meth)acrylic acids and poly(meth)acrylates.

The partial oxidation of propene to acrolein, of isobutene to methacrolein, and the ammoxidation of propene to acrylonitrile are usually carried out by gas phase oxidation in the presence of oxygen and a suitable heterogeneous catalyst. For this purpose, a catalyst based on molybdenum, bismuth, and iron as well as various additives such as nickel, cobalt, tungsten, magnesium, manganese, boron, silicon, and alkali metals, is typically used. Various variations of the catalyst composition are known from the prior art.

These catalysts are customarily produced using relatively complicated processes as described, for example, in U.S. Pat. Nos. 5,856,259, 6,383,973, 6,632,965, 6,781,013, 6,946,422, 7,341,974, 7,544,633, 7,632,777, 7,851,397, US 2010/0323881, and WO 2005/035115 A1, using a slurry of the catalytically active components. The conventional production processes for catalysts typically comprise the following steps: 1. preparation of at least two solutions, 2. production of a slurry by slow mixing of these solutions, 3. drying of the slurry, resulting in a catalyst cake, 4. crushing of the solid material, 5. addition of pore-forming agents, 6. addition of additives for enhancing the mechanical properties, 7. shaping, and 8. calcination.

In addition, these catalysts may be produced by a Pechini process, or a sol-gel process as described, for example, by Bu Young Jo et al. in Appl Catal A:Gen, 358 (2009) 180-185 and Duc Truong Duc et al. in Res Chem Intermed, 37 (2011) 605-616. In these processes, the catalytically active components are dissolved, optionally using a complexing agent, and subsequently gelled under the influence of heat, for example. The customary further steps correspond to steps 3 through 8 mentioned above.

A key feature of all conventional production process is the formation of loose catalytically active material, which must be brought into a certain form or applied to a substrate. It is important to note that the conventional production processes provide loose catalytically active material having a large pore volume, which is detrimental to the mechanical strength of the material. For this reason, in the conventional production processes, additives such as glass fibers for enhancing the mechanical properties must be added to the loose catalytically active material before it is shaped.

The conventional production processes for catalysts for the partial oxidation of olefins also share the common feature that they include precipitation or gelling of the catalytically active components to form a slurry or a gel. It is disadvantageous that a uniform catalyst material is difficult to achieve, since the catalytically active components situated within the solid particles are not able to react with other components that are present in the solution. In addition, the catalytically active components situated within the solid particles are not available for the oxidation reaction to be catalyzed, so that only a small portion of the catalytically active components is in contact with the reaction mixture and thus actually catalyzes the oxidation reaction, which of course not only impairs the efficiency of the catalytically active components that are used, but also decreases the conversion rate of the oxidation reaction to be catalyzed and thus reduces the yield of the desired product.

The object of the present invention, therefore, is to provide a simple and cost-saving method by means of which a highly efficient catalyst may be produced for the partial oxidation of olefins, in particular for the partial oxidation of propene to acrolein, of isobutene to methacrolein, and/or the ammoxidation of propene to acrylonitrile. At the same time, the aim is to overcome the mechanical problems in the shaping on account of the large pore volume of the catalyst which is advantageous for the catalytic effectiveness, without the use of additives for enhancing the mechanical properties, or binders.

This object is achieved by a method for producing a catalyst which includes as the catalytically active component a compound having the general formula $Mo_xBi_yFe_zA_aB_bC_cD_dO_v$, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, y stands for a number from 0.1 to 5, z stands for a number from 0.5 to 5, a stands for a number from 1 to 10, b stands for a number from 0.1 to 6, c stands for a number from $\geq 0$ to 2, d stands for a number from 0.02 to 2, and v is determined by the oxidation state of the elements, the method including the following steps:

a) Providing a solution in which the precursor compounds of the catalytically active component are essentially completely dissolved in a suitable solvent;

b) Bringing the solution obtained in step a) into contact with a (chemically) inert, porous support having a specific surface of 1 to 500 $m^2/g$;

c) Heat treatment of the material obtained in step b), in which the precursor compounds of the catalytically active components are converted to their oxides (i.e. the catalytically active component according to the above formula).

It has surprisingly been found that by bringing a solution containing the precursor compounds of the catalytically active components into contact with a (chemically) inert, porous support without forming a slurry or a gel, a uniform distribution of the catalytically active component in the form of a thin layer on the surface of the support is achieved, so that a supported catalyst is obtained in which essentially all constituents of the catalytically active component are actually available for the oxidation reaction to be catalyzed.

In addition, the problems in the shaping and forming of the required pore structure may be solved by selecting a support which already has a suitable predefined shape and pore structure. At the same time, by selecting a support having high mechanical strength, the problems of mechanical strength are solved without the need for additives for enhancing the mechanical properties, or binders.

The catalyst produced by the method according to the invention comprises as the catalytically active component a compound having the general formula $Mo_xBi_yFe_zA_aB_bC_cD_dO_v$, where A stands for Ni and/or Co, B stands for one or more metals selected from Mg, Cr, Mn, Zn, Ce, and Ca, preferably selected from Mg, Cr, Mn, Zn, and Ca, C stands for W, and D stands for one or more alkali metals Li, Na, K, Cs, Fe, preferably K and/or Cs, where x stands for a number from 10 to 14, in refinements of the invention preferably 12, y stands for a number from 0.1 to 5, z stands for a number from 0.5 to 5, preferably 0.6 to 4, a stands for a number from 1 to 10, b stands for a number from 0.1 to 6, c stands for a number from 0 to 2, d stands for a number from 0.02 to 2, and v is determined by the oxidation state of the other elements. Preferably the catalyst produced according to the invention has the before-mentioned general formula, i.e. consists of the compound of the before-mentioned general formula.

Under the term "compound having the general formula $Mo_xBi_yFe_zA_aB_bC_cD_dO_v$" does not only fall a single compound of the mixed oxide comprising the metals Mo, Bi, Fe, A, B, C, and D, but does also fall a mixture of different oxides comprising 1, 2, 3, 4, 5, 6, or 7 metals selected from the metals of the before-mentioned formula, as long as the ratio of the metals Mo, Bi, Fe, A, B, C, and D is within range of the parameters x, y, z, a, b, c, and d as defined.

In one refinement of the invention, B stands for Mg.

In another refinement of the invention, D stands for K and/or Cs, preferably K.

In another refinement of the invention, y stands for a number from 0.2 to 3, preferably a number from 0.5 to 2 or a number from 0.7 to 1.5, and in another embodiment preferably stands for a number from 0.8 to 1.4, more preferably a number from 0.9 to 1.3, in particular a number from 1.0 to 1.2.

In another refinement of the invention, z stands for a number from 0.6 to 4, preferably a number from 0.7 to 3 or a number from 0.75 to 2.5, in particular a number from 0.8 to 2.2.

In yet another refinement of the invention, a stands for a number from 2 to 9, preferably a number from 3 to 8 or a number from 4 to 7, in particular a number from 5.5 to 6.5.

According to the invention, the molar ratio of Mo to Bi is 140 to 2, preferably 120 to 2.4, and in preferred embodiments of the invention, 15.5 to 7.7 or 13.3 to 9.3. According to the invention, the molar ratio of Bi to Fe is 0.002 to 1, preferably 0.46 to 1.5, and in further embodiments, 1.0 to 1.2 or 0.8 to 2.2.

In another embodiment of the invention, the catalyst produced by the method according to the invention contains Ni as well as Co, the molar fractions e for Ni and f for Co resulting in the sum a, i.e., a=e+f. It is advantageous when e stands for a number from 1.5 to 3.5, preferably a number from 1.8 to 3.2 or a number from 2.0 to 3.0, in particular a number from 2.4 to 2.7, and when f stands for a number from 2.5 to 5.5, preferably a number from 2.8 to 4.5 or a number from 3.0 to 4.0, in particular a number from 3.3 to 3.6.

In another refinement of the invention, b stands for a number from 0.15 to 5, preferably a number from 0.2 to 3 or a number from 0.22 to 2.5, in particular a number from 0.25 to 2.0. For the case that B stands for multiple metals from the group Mg, Cr, Mn, Zn, Ce, and Ca, the molar fractions thereof result in the sum b.

In another refinement of the invention, c stands for a number from 0.02 to 1.5, preferably a number from 0.05 to 1.0 or a number from 0.1 to 0.6, in particular a number from 0.15 to 0.4.

In another refinement of the invention, d stands for a number from 0.03 to 1.0, preferably a number from 0.04 to 0.5 or a number from 0.05 to 0.1, in particular a number from 0.06 to 0.09.

The above-described catalysts produced by the method according to the invention have proven to be particularly suitable for the partial oxidation/ammoxidation of olefins, in particular for the partial oxidation of propene to acrolein, of isobutene to methacrolein, and/or the ammoxidation of propene to acrylonitrile, in particular with regard to a high conversion rate of the starting product and a high yield of the desired products, and at the same time with high selectivity.

In the method according to the invention, a solution in which the precursor compounds of the catalytically active component are essentially completely dissolved in a suitable solvent is provided in a step a). Step a) of the method according to the invention could also be formulated as that the precursor compounds are dissolved in a solvent. The individual precursor compounds of the catalytically active component may be dissolved in a suitable solvent, and/or commercially available, ready-to-use solutions of the individual precursor compounds of the catalytically active component may be used. It is further preferred that all precursor compounds necessary for producing the catalytically active component are already applied in step a) of the method according to the invention.

Within the meaning of the present invention, "precursor compounds of the catalytically active component" mean chemical compounds comprising metals and/or metalloids, which produce an effect in the reaction to be catalyzed. Since the effective forms of the catalytically active component, generally metal oxides and/or metalloid oxides as well as elemental metals and/or metalloids, frequently are sparingly soluble, soluble forms of the corresponding metals and/or metalloids, in particular slightly soluble metal salts and/or metalloid salts, are used as the precursor compounds of the catalytically active component.

Thus, in step a) of the method according to the invention, slightly soluble salts of the precursor compounds of the catalytically active component are preferably used which may be essentially completely dissolved in a suitable solvent.

Within the meaning of the present invention, "essentially completely dissolved" means that at least 95% by weight, preferably at least 98% by weight and particularly preferably at least 99% by weight, of the precursor compounds of the catalytically active component used are dissolved in the solution provided in step a). In other words, the solution provided in step a) of the method according to the invention should be free of residues, apart from technically unavoidable impurities, and thus should represent a clear solution. In order to not compromise the advantages that are achievable using the method according to the invention, the solution provided in step a) of the method according to the invention should not be a slurry, gel, suspension, or other type of dispersion.

The salts which are preferably used as the precursor compounds of the catalytically active component in the method according to the invention are not subject to any special limitations as long as they are soluble in a suitable solvent and include common metal salts or metalloid salts of the corresponding metals or metalloids.

Examples of precursor compounds of the catalytically active component are as follows: Examples of suitable molybdenum compounds include molybdates, in particular ammonium molybdates, preferably ammonium heptamolybdate. Examples of suitable bismuth compounds include inorganic or organic salts of bismuth, in particular bismuth nitrate, bismuth subsalicylate, or bismuth citrate, preferably bismuth nitrate. Examples of suitable iron compounds include inorganic or organic salts of iron(III), in particular iron(III) nitrate, iron(III) salicylate, or iron(III) citrate, preferably iron(III) nitrate. Examples of suitable nickel compounds include nickel acetate, nickel nitrate, nickel salicylate, or nickel citrate, preferably nickel acetate. Examples of suitable cobalt compounds include cobalt acetate, cobalt nitrate, cobalt salicylate, or cobalt citrate, preferably cobalt acetate. Examples of suitable magnesium compounds include magnesium acetate, magnesium nitrate, magnesium salicylate, or magnesium citrate, preferably magnesium acetate. Examples of suitable tungsten compounds include tungstates, in particular ammonium tungstates, preferably ammonium metatungstate. Examples of suitable potassium compounds include potassium acetate, potassium nitrate, potassium salicylate, or potassium citrate, preferably potassium acetate. Examples of suitable cesium compounds include cesium acetate, cesium nitrate, cesium salicylate, or cesium citrate, preferably cesium acetate. According to the so-called Pearson hard and soft acids and bases (HSAB) concept, cesium ($Cs^+$) is a so-called "soft" cation, and according to the invention is better suited than a "hard" cation such as $Li^+$ or $Na^+$. Other suitable salts of the above-mentioned metals as well as salts of other metals, for example chromium, manganese, zinc, cerium, and/or calcium, and/or of metalloids may be easily selected by those skilled in the art. Mixtures of various salts of the same metal may also be used.

It is advantageous when the counterion of the salts of the precursor compounds of the catalytically active component which are preferably used in the method according to the invention, i.e., generally the anion, or in the case of metal acids such as tungstate or molybdate, the cation, may be removed with essentially no residues in the heat treatment in step c) of the method according to the invention.

In another embodiment of the present invention, an aqueous solvent is used as the suitable solvent in step a) of the method according to the invention, i.e., a solvent composed of water, or a solvent mixture which in addition to water contains one or more further solvents that are miscible with water, such as polar organic solvents, in particular alcohols. The use of an aqueous solvent in step a) of the method according to the invention is advantageous from an environmental and economic standpoint.

It is also preferred for the aqueous solvent to include an acidic aqueous solvent, by means of which the complete dissolution of the precursor compounds of the catalytically active component is facilitated in many cases. This is specifically advantageous in that Bi precursor compounds and Mo precursor compounds are usually not soluble in one solution under the same conditions. However, the means for acidifying the aqueous solvent is not subject to any special limitations as long as it is suitable for solving all precursor compounds in one solution, and as long as it does not impair the catalytic activity of the finished catalyst. In this regard, in particular acids are preferred which may be removed with essentially no residues in the heat treatment in step c) of the method according to the invention. By using an acid for ensuring that all of the precursor compounds can be solved has the technical effect that the particle growth is very low resulting in a relatively high BET-surface area. Another advantage of a homogeneous solution of the precursor compounds is that all of the metals of the catalytically active component are evenly distributed over the entire catalyst. The latter advantage cannot be reached when no acid is added. The other advantages can only partly be compensated in that the precipitated powder is spray-calcined in a pulsation reactor instead of a simple calcination in an oven.

The before-mentioned acids may be inorganic or organic acids. Organic acids are more preferred in the method according to the invention. It is even more preferred that the organic acid is a weak organic acid such as glycolic acid, acetic acid, lactic acid, citric acid, oxalic acid, malonic acid, succinic acid, adipic acid, maleic acid, tartaric acid, or mixtures thereof, in particular glycolic acid, acetic acid, and/or lactic acid. It is further preferred that the organic acid is a chelating organic acid, i.e. be capable to stabilize the metals of the precursor compounds of the catalytically active component by means of more than one coordinative bond. These chelating organic acids are preferably α-hydroxycarboxylic acids, dicarboxylic acids. Preferred examples of such chelating organic acids are glycolic acid, lactic acid, citric acid, oxalic acid, malonic acid, succinic acid, adipic acid, maleic acid, tartaric acid, or mixtures thereof, in particular glycolic acid, and/or lactic acid. The latter allows better solubilization of the metals and metal bonds. An advantageous pH of the acidic aqueous solvent is in the range of pH 0 to 6, preferably pH 0.5 to 4, taking into account the fact that some metallic precursor compounds of the catalytically active component are only sparingly or slowly soluble in a neutral or weakly basic environment, while other metallic precursor compounds of the catalytically active component may precipitate in an excessively acidic environment. A suitable pH may be easily selected by those skilled in the art, taking into account the particular precursor compounds of the catalytically active component to be used.

In the method according to the invention, the solution obtained in step a) is brought into contact with a chemically inert, porous support having a specific surface of 1 to 500 $m^2/g$ (measured according to the BET method of DIN ISO 9277:2010 or DIN 66134) in a step b).

In one preferred embodiment, step b) includes impregnation of the (chemically) inert, porous support with the solution obtained in step a). The impregnation is particularly preferably carried out using a so-called incipient wetness method (pore-filling method) in which the porous support is combined with a volume of the solution obtained in step a) which corresponds to its pore volume. It is advantageous for the porous support to contain no water residues prior to the impregnation, so that the support material is preferably dried prior to the impregnation in order to remove any water from the pores and thus increase the free pore volume. In this method, the catalytically active component and the precursor compounds thereof are distributed very uniformly on the surface of the support.

In another embodiment, step b) includes coating of the surface of the chemically inert, porous support with the solution obtained in step a). Examples of coating methods preferred according to the invention include spraying the solution obtained in step a) onto the support (spray coating) and dipping the support into the solution obtained in step a) (dip coating).

In another embodiment, the support is heated during the bringing into contact according to step b) of the method according to the invention and/or directly thereafter in order to rapidly evaporate the solvent. This is advantageous in particular when runoff of the solution is to be avoided. On the other hand, it may also be advantageous to delay the evaporation of the solvent, for example by cooling the support, when a uniform distribution of the catalytically active component or the precursor compounds of the catalytically active component cannot be ensured.

It is important for the method according to the invention that the porous support has a certain specific surface in order to ensure a high conversion rate of the oxidation reaction to be catalyzed, and thus, a high yield of the desired product. This is because the pore structure of the support, among other factors, primarily determines the pore structure of the finished catalyst. According to the invention, the specific surface of the support is 1 to 500 m²/g, preferably 1 to 250 m²/g, preferably 1 to 100 m²/g, more preferably 2 to 90 m²/g, even more preferably 5 to 85 m²/g, most preferably 10 to 80 m²/g. The specific surface is determined using the BET method according to DIN ISO 9277:2010.

In one preferred embodiment, the inert, porous support, preferably chemically inert support, is formed as a molded body. In principle, the support formed as a molded body may have any shape known by those skilled in the art to be suitable for the purpose according to the invention. As the result of forming the support into the shape desired for the subsequent use in the reaction to be catalyzed prior to bringing it into contact with the precursor compounds of the catalytically active component, shaping the catalyst before the calcination, as is known from the prior art, is no longer necessary, so that the mechanical problems of the catalysts from the prior art do not occur in the shaping in the method according to the invention, also without the need for using additives for enhancing the mechanical properties, or binders.

The support material is not subject to any special limitations as long as it is (chemically) inert and has the required specific surface. Within the meaning of the present invention, "inert" or "chemically inert" means that during the reaction to be catalyzed, the support material does not take part in a chemical reaction, in particular with substances participating in the reaction to be catalyzed.

In one preferred embodiment, the support material according to the invention is an inorganic support material. Suitable examples include silicon carbide, silicon dioxide, zirconium dioxide, titanium dioxide, aluminum oxide, porous ceramics, sheet silicates, bentonites, and mixtures thereof. Supports that are not inorganic, in particular carbon-based supports, may also be used.

According to another embodiment of the method according to the invention, it may be provided that a drying step takes place between step b) and step c) of the method according to the invention. This optional drying step is used to remove the solvent, so that, in contrast to the heat treatment according to step c) of the method according to the invention, the precursor compounds of the catalytically active component are not appreciably decomposed into their oxides. The drying temperature is preferably in the range of 25 to 250° C., preferably in the range of 50 to 200° C., more preferably in the range of 80 to 180° C., and particularly preferably in the range of 100 to 150° C. The drying period is preferably in the range of 5 min to 10 h, preferably in the range of 30 min to 8 h, more preferably in the range of 1 to 5 h.

In the method according to the invention, the material obtained in step b) which is optionally subjected to a drying step undergoes heat treatment in a step c), so that the precursor compounds of the catalytically active component are decomposed into their oxides (i.e. the catalytically active component).

In one preferred embodiment, step c) of the method according to the invention includes calcination of the material obtained in step b) which is optionally subjected to a drying step. The term "calcination" is generally understood to mean heating to high temperatures with the objective of changing, in particular materially or structurally, the treated material or a component thereof. As the result of calcination, for example thermal decomposition, a phase transition, or the removal of volatile substances may be achieved. In step c) of the method according to the invention, in particular the precursor compounds of the catalytically active component, which have been used in soluble form in step a) of the method according to the invention as stated above, are decomposed into their respective oxides, i.e., converted to their catalytically effective form.

In one particularly preferred embodiment, the heat treatment according to step c) of the method according to the invention includes heating of the material obtained in step b), which is optionally subjected to a drying step, to a temperature in the range of 400 to 700° C., preferably in the range of 450 to 650° C., more preferably in the range of 480 to 620° C., and particularly preferably in the range of 500 to 610° C. The duration of the heat treatment according to step c) of the method according to the invention is preferably in the range of 30 min to 20 h, preferably in the range of 45 min to 15 h, more preferably in the range of 1 to 8 h.

The present invention further relates to a catalyst which is obtainable using the method according to the invention. The catalyst according to the invention not only has a high efficiency of the catalytically active components used, since essentially all catalytically active components used are actually available for the reaction to be catalyzed, but also has a high conversion rate of the reaction to be catalyzed and thus a high yield of the desired product, since, due to the targeted selection of the catalyst support, the pore structure of the product may be optimally adjusted to the needs of the reaction to be catalyzed The catalyst according to the invention is very well suited in particular for the partial oxidation/ammoxidation of olefins, in particular for the partial oxidation of propene to acrolein, of isobutene to methacrolein, and/or the ammoxidation of propene to acrylonitrile.

The catalyst according to the invention includes a compound having the general formula $Mo_xBi_yFe_zA_aB_bC_cD_dO_v$ as the catalytically active component, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, and in preferred refinements x is 12, y stands for a number from 0.1 to 5, z stands for a number from 0.5 to 5, a stands for a number from 1 to 10, b stands for a number from 0.1 to 6, c stands for a number from ≥0 to 2, d stands for a number from 0.02 to 2, and v is determined by the oxidation state of the other elements.

In one refinement of the invention, B stands for Mg.

In another refinement of the invention, D stands for K and/or Cs, preferably K.

In another refinement of the invention, y stands for a number from 0.2 to 3, preferably a number from 0.5 to 2 or a number from 0.7 to 1.5, more preferably a number from 0.8 to 1.4, even more preferably a number from 0.9 to 1.3, in particular a number from 1.0 to 1.2.

In another refinement of the invention, z stands for a number from 0.6 to 4, preferably a number from 0.7 to 3 or a number from 0.75 to 2.5, in particular a number from 0.8 to 2.2.

In yet another refinement of the invention, a stands for a number from 2 to 9, preferably a number from 3 to 8 or a number from 4 to 7, in particular a number from 5.5 to 6.5.

In another embodiment, the catalyst according to the invention contains Ni as well as Co, the molar fractions e for Ni and f for Co resulting in the sum a, i.e., a=e+f. It is advantageous when e stands for a number from 1.5 to 3.5, preferably a number from 1.8 to 3.2, more preferably a number from 2.0 to 3.0, in particular a number from 2.4 to 2.7, and when f stands for a number from 2.5 to 5.5, preferably a number from 2.8 to 4.5 or a number from 3.0 to 4.0, in particular a number from 3.3 to 3.6.

In another refinement of the invention, b stands for a number from 0.15 to 5, preferably a number from 0.2 to 3 or a number from 0.22 to 2.5, in particular a number from 0.25 to 2.0. For the case that B stands for multiple metals from the group Mg, Cr, Mn, Zn, Ce, and Ca, the molar fractions thereof result in the sum b.

In another refinement of the invention, c stands for a number from 0.02 to 1.5, preferably a number from 0.05 to 1.0 or a number from 0.1 to 0.6, in particular a number from 0.15 to 0.4.

In another refinement of the invention, d stands for a number from 0.03 to 1.0, preferably a number from 0.04 to 0.5 or a number from 0.05 to 0.1, in particular a number from 0.06 to 0.09.

The above-described catalysts according to the invention have proven to be particularly suitable for the partial oxidation/ammoxidation of olefins, in particular for the partial oxidation of propene to acrolein, of isobutene to methacrolein, and/or the ammoxidation of propene to acrylonitrile, in particular with regard to a high conversion rate of the starting product and a high yield of the desired products, and at the same time with high selectivity.

Accordingly, the present invention further relates to the use of a catalyst according to the invention for the partial oxidation or ammoxidation of olefins, in particular for the oxidation of propene to acrolein or of isobutene to methacrolein, and/or for the ammoxidation of propene to acrylonitrile.

Furthermore, the present invention also relates to a method for the partial oxidation or ammoxidation of olefins, in particular the oxidation of propene to acrolein or of isobutene to methacrolein, and/or ammoxidation of propene to acrylonitrile, wherein in a first step a catalyst is produced according to the method of the present invention and in a second step the partial oxidation or ammoxidation of olefins is applied with that catalyst.

The present invention further relates to the following embodiments:

In an embodiment (i) the present invention relates to a method for producing a catalyst which includes as the catalytically active component a compound having the general formula $Mo_xBi_yFe_zA_aB_bC_cD_dO_v$, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, y stands for a number from 0.1 to 5, z stands for a number from 0.5 to 5, a stands for a number from 1 to 10, b stands for a number from 0.1 to 6, c stands for a number from ≥0 to 2, d stands for a number from 0.02 to 2, and v is determined by the oxidation state of the elements, the method including the following steps:
  a) Providing a solution in which the catalytically active components are essentially completely dissolved in a suitable solvent;
  b) Bringing the solution obtained in step a) into contact with a chemically inert, porous support having a specific surface of 1 to 500 m²/g;
  c) Heat treatment of the material obtained in step b), in which the catalytically active components are converted to their oxides.

In another embodiment (ii) the present invention relates to a method according to embodiment (i), wherein step b) includes impregnation of the chemically inert, porous support with the solution obtained in step a).

In another embodiment (iii) the present invention relates to a method according to embodiment (i), wherein step b) includes coating of the surface of the chemically inert, porous support with the solution obtained in step a).

In another embodiment (iv) the present invention relates to a method according to one of the preceding embodiments (i) to (iii), wherein the chemically inert, porous support has a specific surface of 1 to 100 m²/g.

In another embodiment (v) the present invention relates to a method according to one of the preceding embodiments (i) to (iv), wherein the chemically inert, porous support is formed as a molded body.

In another embodiment (vi) the present invention relates to a method according to one of the preceding embodiments (i) to (v), wherein the chemically inert, porous support is an inorganic support.

In another embodiment (vii) the present invention relates to a method according to one of the preceding embodiments (i) to (vi), wherein step c) includes calcination of the material obtained in step b).

In another embodiment (viii) the present invention relates to a method according to one of the preceding embodiments (i) to (vii), wherein the heat treatment in step c) includes heating the material obtained in step b) to a temperature of 450 to 650° C. over a period of 1 to 8 hours.

In another embodiment (ix) the present invention relates to a method according to one of the preceding embodiments (i) to (viii), wherein the suitable solvent in step a) is an aqueous solvent, in particular an acidic aqueous solvent.

In another embodiment (x) the present invention relates to a catalyst which includes a compound having the general formula $Mo_xBi_yFe_zA_aB_bC_cD_dO_v$ as the catalytically active component, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, and in preferred refinements x is 12, y stands for a number from 0.1 to 5, z stands for a number from 0.5 to 5, a stands for a number from 1 to 10, b stands for a number from 0.1 to 6, c stands for a number from ≥0 to 2, d stands for a number from 0.02 to 2, and v is determined by the oxidation state of the other elements, the catalyst being obtainable by a method according to one of the preceding embodiments (i) to (ix).

In another embodiment (xi) the present invention relates to the catalyst according to embodiment (x), where x is 12.

In another embodiment (xii) the present invention relates to the use of a catalyst according to embodiments (x) and (xi) for the partial oxidation or ammoxidation of olefins, in particular for the oxidation of propene to acrolein and/or of isobutene to methacrolein, and/or for the ammoxidation of propene to acrylonitrile.

The term "catalytically active components" in steps a) to c) of the method according to embodiment (i) is to be understood as precursor compounds of the catalytically active component in the meaning as defined above.

The invention is explained in greater detail below with reference to several exemplary embodiments, which are not to be construed as limiting to the scope of the invention.

EXAMPLES

Example 1

0.512 g bismuth nitrate, 2.118 g ammonium heptamolybdate, 0.610 g nickel acetate, 0.82 g cobalt acetate, 0.483 g iron(III) nitrate, and 0.43 g magnesium acetate were dissolved in 3 mL of an aqueous glycolic acid solution (70% by weight in water). After dissolution was complete, 0.111 mL of an ammonium metatungstate solution (2.35 M tungsten) and 0.062 mL of a potassium acetate solution (1.13 M) were added. This solution was mixed with 6 g SiC (BET=27 m$^2$/g, pore volume: 0.9 mL/g). The material obtained was calcined for 4 hours at 500° C., resulting in catalyst 1.

Example 2

0.512 g bismuth nitrate, 2.118 g ammonium heptamolybdate, 0.610 g nickel acetate, 0.82 g cobalt acetate, 0.322 g iron(III) nitrate, and 0.43 g magnesium acetate were dissolved in 3 mL of an aqueous glycolic acid solution (70% by weight in water). After dissolution was complete, 0.128 mL of an ammonium metatungstate solution (2.35 M tungsten) and 0.062 mL of a potassium acetate solution (1.13 M) were added. This solution was mixed with 6 g SiC (BET=27 m$^2$/g, pore volume: 0.9 mL/g). The material obtained was calcined for 4 hours at 500° C., resulting in catalyst 2.

Example 3

0.256 g bismuth nitrate, 1.059 g ammonium heptamolybdate, 0.305 g nickel acetate, 0.41 g cobalt acetate, 0.402 g iron(III) nitrate, and 0.215 g magnesium acetate were dissolved in 3 mL of an aqueous glycolic acid solution (70% by weight in water). After dissolution was complete, 0.085 mL of an ammonium metatungstate solution (2.35 M tungsten) and 0.031 mL of a potassium acetate solution (1.13 M) were added. This solution was mixed with 3 g SiC (BET=27 m$^2$/g, pore volume: 0.9 mL/g). The material obtained was calcined for 4 hours at 500° C., resulting in catalyst 3.

Example 4

0.256 g bismuth nitrate, 1.059 g ammonium heptamolybdate, 0.305 g nickel acetate, 0.41 g cobalt acetate, 0.402 g iron(III) nitrate, and 0.108 g magnesium acetate were dissolved in 1.5 mL of an aqueous glycolic acid solution (70% by weight in water). After dissolution was complete, 0.043 mL of an ammonium metatungstate solution (2.35 M tungsten) and 0.031 mL of a potassium acetate solution (1.13 M) were added. This solution was mixed with 3 g SiC (BET=27 m$^2$/g, pore volume: 0.9 mL/g). The material obtained was calcined for 4 hours at 500° C., resulting in catalyst 4.

Example 5

0.256 g bismuth nitrate, 1.0593 g ammonium heptamolybdate, 0.305 g nickel acetate, 0.41 g cobalt acetate, 0.402 g iron(III) nitrate, and 0.215 g magnesium acetate were dissolved in 1.5 mL of an aqueous glycolic acid solution (70% by weight in water). After dissolution was complete, 0.043 mL of an ammonium metatungstate solution (2.35 M tungsten) and 0.031 mL of a potassium acetate solution (1.13 M) were added. This solution was mixed with 3 g SiC (BET=27 m$^2$/g, pore volume: 0.9 mL/g). The material obtained was calcined for 4 hours at 500° C., resulting in catalyst 5.

Example 6

0.261 g bismuth nitrate, 1.0593 g ammonium heptamolybdate, 0.311 g nickel acetate, 0.418 g cobalt acetate, 0.41 g iron(III) nitrate, and 0.110 g magnesium acetate were dissolved in 1.5 mL of an aqueous glycolic acid solution (70% by weight in water). After dissolution was complete, 0.043 mL of an ammonium metatungstate solution (2.35 M tungsten) and 0.032 mL of a potassium acetate solution (1.13 M) were added. This solution was mixed with 2.2 g SiO$_2$ (BET=68 m$^2$/g, pore volume: 1.2 mL/g). The material obtained was calcined for 4 hours at 500° C., resulting in catalyst 6.

Example 7

0.261 g bismuth nitrate, 1.0593 g ammonium heptamolybdate, 0.311 g nickel acetate, 0.418 g cobalt acetate, 0.41 g iron(III) nitrate, and 0.110 g magnesium acetate were dissolved in 1.5 mL of an aqueous glycolic acid solution (70% by weight in water). After dissolution was complete, 0.043 mL of an ammonium metatungstate solution (2.35 M tungsten) and 0.032 mL of a potassium acetate solution (1.13 M) were added. This solution was mixed with 2.2 g SiO$_2$ (BET=68 m$^2$/g, pore volume: 1.2 mL/g). The material obtained was calcined for 3 hours at 550° C., resulting in catalyst 7.

Example 8

0.279 g bismuth nitrate, 1.0593 g ammonium heptamolybdate, 0.332 g nickel acetate, 0.447 g cobalt acetate, 0.439 g iron(III) nitrate, and 0.030 g magnesium acetate were dissolved in 1.5 mL of an aqueous glycolic acid solution (70% by weight in water). After dissolution was complete, 0.039 mL of an ammonium metatungstate solution (2.35 M tungsten) and 0.034 mL of a potassium acetate solution (1.13 M) were added. This solution was mixed with 2.2 g SiO$_2$ (BET=68 m$^2$/g, pore volume: 1.2 mL/g). The material obtained was calcined for 1 hour at 550° C., resulting in catalyst 8.

Example 9

0.261 g bismuth nitrate, 1.0593 g ammonium heptamolybdate, 0.311 g nickel acetate, 0.418 g cobalt acetate, 0.41 g iron(III) nitrate, and 0.110 g magnesium acetate were dissolved in 1.5 mL of an aqueous glycolic acid solution (70% by weight in water). After dissolution was complete, 0.043 mL of an ammonium metatungstate solution (2.35 M tungsten) and 0.032 mL of a potassium acetate solution (1.13 M) were added. This solution was mixed with 3 g SiC (BET=27 m$^2$/g, pore volume: 0.9 mL/g). The material obtained was calcined for 1 hour at 590° C., resulting in catalyst 9.

Example 10

0.279 g bismuth nitrate, 1.0593 g ammonium heptamolybdate, 0.332 g nickel acetate, 0.447 g cobalt, 0.439 g iron(III) nitrate, and 0.030 g magnesium acetate were dissolved in 1.5 mL of an aqueous glycolic acid solution (70% by weight in water). After dissolution was complete, 0.039 mL of an ammonium metatungstate solution (2.35 M tungsten) and 0.034 mL of a potassium acetate solution (1.13 M) were added. This solution was mixed with 3 g SiC (BET=27 m$^2$/g, pore volume: 0.9 mL/g). The material obtained was calcined for 1 hour at 590° C., resulting in catalyst 10.

Example 11

0.256 g bismuth nitrate, 1.059 g ammonium heptamolybdate, 0.305 g nickel acetate, 0.41 g cobalt acetate, 0.402 g iron(III) nitrate, and 0.108 g magnesium acetate were dissolved in 1.5 mL of an aqueous lactic acid solution (70% by weight in water). After dissolution was complete, 0.043 mL of an ammonium metatungstate solution (2.35 M tungsten) and 0.031 mL of a potassium acetate solution (1.13 M) were added. This solution was mixed with 3 g SiC (BET=27 m$^2$/g). The material obtained was calcined for 4 hours at 500° C., resulting in catalyst 11.

COMPARATIVE EXAMPLES

Comparative Example 1

0.256 g bismuth nitrate, 1.059 g ammonium heptamolybdate, 0.305 g nickel acetate, 0.41 g cobalt acetate, 0.402 g iron(III) nitrate, and 0.108 g magnesium acetate were dissolved in 1.5 mL of an aqueous glycolic acid solution (70% by weight in water). After dissolution was complete, 0.043 mL of an ammonium metatungstate solution (2.35 M tungsten) and 0.031 mL of a potassium acetate solution (1.13 M) were added. This solution was mixed with 3 g SiC (BET=0.001 m$^2$/g). The material obtained was calcined for 4 hours at 500° C., resulting in catalyst 12.

Comparative Example 2

0.256 g bismuth nitrate, 1.059 g ammonium heptamolybdate, 0.305 g nickel acetate, 0.41 g cobalt acetate, 0.402 g iron(III) nitrate, and 0.108 g magnesium acetate were dissolved in 1.5 mL of an aqueous glycolic acid solution (70% by weight in water). After dissolution was complete, 0.043 mL of an ammonium metatungstate solution (2.35 M tungsten) and 0.031 mL of a potassium acetate solution (1.13 M) were added. This solution was mixed with 3 g α-Al$_2$O$_3$ (BET=0.1 m$^2$/g). The material obtained was calcined for 4 hours at 500° C., resulting in catalyst 13.

Comparative Example 3

A first solution was prepared by dissolving 0.44 g ammonium heptamolybdate and 0.018 g ammonium metatungstate in 0.89 mL water and adding 0.065 g colloidal SiO$_2$ (BET=129-155 m$^2$/g; Ludox AS-40). A second solution was prepared by dissolving 0.0149 g bismuth nitrate, 0.312 g nickel nitrate, 0.089 g cobalt nitrate, 0.185 g ferric nitrate, 0.118 g magnesium nitrate, 0.00032 g potassium nitrate, and 0.00061 g cesium nitrate in 0.62 mL water. The two aqueous solutions were combined to form a slurry. To the slurry was added 0.046 g of Coconit 300. The slurry was dried on a hot plate and the solid was further dried at 110° C. The solid was calcined in air at 580° C. for 1 h to produce catalyst 14.

The elemental composition of the obtained material was as follows:

$Mo_{12}Bi_{0.15}Fe_{2.21}Ni_{5.15}Co_{1.47}Mg_{2.21}W_{0.37}K_{0.01}Cs_{0.015}Si_{5.2}$

Comparative Example 4

A first solution was prepared by dissolving 0.44 g ammonium heptamolybdate in 0.89 mL water and adding 0.065 g colloidal SiO$_2$ (BET=129-155 m$^2$/g; Ludox AS-40). A second solution was prepared by dissolving 0.0286 g bismuth nitrate, 0.24 g nickel nitrate, 0.137 g cobalt nitrate, 0.143 g ferric nitrate, 0.090 g magnesium nitrate, 0.030 g manganese nitrate, 0.030 g cerium nitrate, 0.00023 g potassium nitrate, and 0.00093 g cesium nitrate in 0.83 mL water. The two aqueous solutions were combined to form a slurry. To the slurry was added 0.046 g of Coconit 300. The slurry was dried on a hot plate and the solid was further dried at 110° C. The solid was calcined in air at 580° C. for 1 h to produce catalyst 15.

The elemental composition of the obtained material was as follows:

$Mo_{12}Bi_{0.28}Fe_{1.7}Ni_{3.97}Co_{2.27}Mg_{1.7}Mn_{0.57}Ce_{0.34}K_{0.011}Cs_{0.023}Si_{5.2}$

The elemental composition of the obtained catalysts is summarized in Table 1 below.

Comparative Example 5

A first solution is produced in that 1.02 kg iron nitrate nonahydrate (Honeywell; Lot: B 1960) is added to 0.727 kg deionized water at 60° C. Without further heating the solution 2.37 kg nickel nitrate hexahydrate (ALFA Aesar; Lot: 61101000) and 0.62 kg magnesium nitrate hexahydrate (Honeywell; Lot: 90140) are subsequently added, and the compounds are solved under stirring. Then, 0.039 kg 1 M KOH (Merck; Lot: HC111978) is added. After the addition of KOH a brown precipitate is formed, which is then again quickly solved. Subsequently, 0.3 kg bismuth nitrate pentahydrate (ALFA Aesar; Lot: 42060004) is added.

A second solution is produced by adding 2.62 kg ammoniumheptamolybdat tetrahydrat (HC Starck; Lot: 1163/048) into 8.3 kg deionized water and is solved under stirring.

After that, the first and the second solution are combined and 0.19 kg Syloid C809 (Grace Davison; Lot: 1000214955; colloidal SiO$_2$) is added. Thereby, a precipitate is formed which forms a suspension with the resulting solution.

The so obtained suspension is spray-calcined in a pulsation reactor of the company IBU-tec (Typ: PR-4). The temperature in the pulsation reactor is 500° C. and the residence time was in the range of 200 ms to 2 s. The obtained material is formed to catalyst 16.

TABLE 1

| Catalyst | Mo | Bi | Fe | Ni | Co | Mg | W | K |
|---|---|---|---|---|---|---|---|---|
| Catalyst 1 | 12 | 1.05 | 1.2 | 2.45 | 3.3 | 2.0 | 0.26 | 0.07 |
| Catalyst 2 | 12 | 1.05 | 0.8 | 2.45 | 3.3 | 2.0 | 0.3 | 0.07 |
| Catalyst 3 | 12 | 1.05 | 2.0 | 2.45 | 3.3 | 2.0 | 0.4 | 0.07 |
| Catalyst 4 | 12 | 1.05 | 2.0 | 2.45 | 3.3 | 1.0 | 0.2 | 0.07 |
| Catalyst 5 | 12 | 1.05 | 2.0 | 2.45 | 3.3 | 2.0 | 0.2 | 0.07 |
| Catalyst 6 | 12 | 1.07 | 2.04 | 2.5 | 3.37 | 1.02 | 0.2 | 0.07 |
| Catalyst 7 | 12 | 1.07 | 2.04 | 2.5 | 3.37 | 1.02 | 0.2 | 0.07 |
| Catalyst 8 | 12 | 1.145 | 2.18 | 2.67 | 3.6 | 0.28 | 0.185 | 0.08 |
| Catalyst 9 | 12 | 1.07 | 2.04 | 2.5 | 3.37 | 1.02 | 0.2 | 0.07 |
| Catalyst 10 | 12 | 1.145 | 2.18 | 2.67 | 3.6 | 0.28 | 0.185 | 0.08 |
| Catalyst 11 | 12 | 1.05 | 2.0 | 2.45 | 3.3 | 1.0 | 0.2 | 0.07 |
| Catalyst 12 | 12 | 1.05 | 2.0 | 2.45 | 3.3 | 1.0 | 0.2 | 0.07 |
| Catalyst 13 | 12 | 1.05 | 2.0 | 2.45 | 3.3 | 1.0 | 0.2 | 0.07 |

Test Results:

Catalysts 1 through 16 were tested with regard to their catalytic properties in the partial oxidation of propene. For this purpose, they were added to a multi-channel fixed-bed reactor and exposed to a reaction mixture composed of 8% by volume propene, 14.4% by volume oxygen, 8% by volume water vapor, 10% by volume neon, and the remainder helium at 360° C. for a contact period of 0.5 to 2.5 sec. The results obtained are shown in Table 2 below.

TABLE 2

| Catalyst | Propylene conversion rate [%] | Yield (acrolein and acrylic acid) [%] |
|---|---|---|
| Catalyst 1 | 99.0 | 95.6 |
| Catalyst 2 | 99.1 | 95.8 |
| Catalyst 3 | 99.1 | 94.6 |
| Catalyst 4 | 99.5 | 96.1 |
| Catalyst 5 | 99.2 | 93.9 |
| Catalyst 6 | 99.0 | 96.3 |
| Catalyst 7 | 99.1 | 96.2 |
| Catalyst 8 | 99.0 | 96.2 |
| Catalyst 9 | 98.4 | 95.9 |
| Catalyst 10 | 98.0 | 95.8 |
| Catalyst 11 | 98.6 | 95.9 |
| Catalyst 12* | 2.8 | 2.75 |
| Catalyst 13* | 13.8 | 13.3 |
| Catalyst 14* | 91.8 | 96.0 |
| Catalyst 15* | 87.8 | 94.1 |
| Catalyst 16* | 99.5 | 88.6 |

*Comparative examples

These results clearly show that the catalysts produced by the method according to the invention are highly effective, selective catalysts for the oxidation of olefins. The catalysts of the comparative examples, in which the same solution was used as for catalyst 4 according to the invention but in which a support not according to the invention, having a low specific surface, was used, are clearly inferior to the catalysts according to the invention, and can by no means be used to achieve the underlying object of the present invention. Catalyst 16 is prepared according to the invention with the only difference that no chelating acid is used in the solution comprising all metal precursor compounds. The use of the pulsating temperature treatment, however, ensures that the disadvantage of the absence of a chelating acid is partly compensated in the catalytic performance. However, when preparing a catalyst according to comparative example 5 but calcining the material at about 550° C. for 1 h in a usual calcining oven instead of the pulsating treatment, the inventors of the present invention observed that the catalytic performance is significantly lower than for catalyst 16.

The invention claimed is:

1. A method for producing a catalyst which includes as the catalytically active component a compound having the general formula $Mo_xBi_yFe_zA_aB_bC_cD_dO_v$, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, y stands for a number from 0.1 to 5, z stands for a number from 0.5 to 5, a stands for a number from 1 to 10, b stands for a number from 0.1 to 6, c stands for a number from ≥0 to 2, d stands for a number from 0.02 to 2, and v is determined by the oxidation state of the elements, the method including the following steps:
a) providing a solution in which all precursor compounds of the Mo, Bi, Fe, A, B, C and D components of the catalytically active component are essentially completely dissolved in a suitable solvent;
b) bringing the solution obtained in step a) into contact with a chemically inert, porous support having a specific surface of 1 to 500 m²/g; and
c) heat treatment of the material obtained in step b), in which the precursor compounds of the catalytically active component are converted to their oxides.

2. The method according to claim 1, wherein step b) includes impregnation of the chemically inert, porous support with the solution obtained in step a).

3. The method according to claim 1, wherein step b) includes coating of the surface of the chemically inert, porous support with the solution obtained in step a).

4. The method according to claim 1, wherein the chemically inert, porous support has a specific surface of 1 to 100 m²/g.

5. The method according to claim 1, wherein the chemically inert, porous support is formed as a molded body.

6. The method according to claim 1, wherein the chemically inert, porous support is an inorganic support.

7. The method according to claim 1, wherein step c) includes calcination of the material obtained in step b).

8. The method according to claim 1, wherein the heat treatment in step c) includes heating the material obtained in step b) to a temperature of 450 to 650° C. over a period of 1 to 8 hours.

9. The method according to claim 1, wherein the suitable solvent in step a) is an aqueous solvent.

10. A catalyst which includes a compound having the general formula $Mo_xBi_yFe_zA_aB_bC_cD_dO_v$ as the catalytically active component, where A stands for Ni and/or Co, B stands for one or more metals selected from Mg, Cr, Mn, Zn, Ce, and Ca and combinations thereof, C stands for W, and D stands for one or more alkali metals, where x stands for a number from 10 to 14, y stands for a number from 0.1 to 5, z stands for a number from 0.5 to 5, a stands for a number from 1 to 10, b stands for a number from 0.1 to 6, c stands for a number from ≤0 to 2, d stands for a number from 0.02 to 2, and v is determined by the oxidation state of the other elements, the catalyst being obtainable by a method according to claim 1.

11. The catalyst according to claim 10, where x is 12.

12. A process for the partial oxidation or ammoxidation of olefins, the process comprising oxidizing or ammoxidating an olefin in contact with a catalyst according to claim 10.

13. The process according to claim 12, wherein partial oxidation or ammoxidation of olefins is an oxidation of propene to acrolein, an ammoxidation of propene to acrylonitrile, or an oxidation of isobutene to methacrolein.

14. The method according to claim 1, wherein
the suitable solvent in step a) is an aqueous solvent;
step b) includes impregnation of or coating the surface of the chemically inert, porous support with the solution obtained in step a),
the chemically inert, porous support is an inorganic support having a specific surface of 1 to 100 m²/g; and
step c) includes calcination of the material obtained in step b).

15. The method according to claim 14, wherein the heat treatment in step c) includes heating the material obtained in step b) to a temperature of 450 to 650° C. over a period of 1 to 8 hours.

16. The method according to claim 1, wherein at least 99% by weight of the precursor compounds of the precursor compounds of the catalytically active component are dissolved in the solution of step a).

17. The method according to claim 1, wherein x is 12, y is 0.7 to 1.5, z is 0.7 to 3, a is 2 to 9, c is 0.05 to 1.0, and d is 0.04 to 0.5.

18. The method according to claim 17, wherein the molar ratio of Mo to Bi is 15.5 to 7.7.

19. The method according to claim 18, wherein the molar ratio of Bi to Fe is 0.46 to 1.5.

20. The method according to claim 17, wherein A includes Ni and Co.

* * * * *